(12) United States Patent
Yasui et al.

(10) Patent No.: US 6,320,393 B1
(45) Date of Patent: Nov. 20, 2001

(54) FLUID DIELECTRIC CONSTANT SENSING DEVICE AND METHOD EMPLOYING THE SAME

(75) Inventors: Katsuaki Yasui; Mitsuhiro Ono, both of Tokyo; Susumu Nagano, Hyogo, all of (JP)

(73) Assignee: Mitsubishi Denki Kabushiki Kaisha, Tokyo (JP)

( * ) Notice: Subject to any disclaimer, the term of this patent is extended or adjusted under 35 U.S.C. 154(b) by 0 days.

(21) Appl. No.: 09/271,429

(22) Filed: Mar. 18, 1999

(30) Foreign Application Priority Data

Oct. 20, 1998 (JP) .................................................. 10-298448

(51) Int. Cl.[7] .................................................. G01R 27/26
(52) U.S. Cl. ............................................................ 324/663
(58) Field of Search ..................................... 324/694, 654, 324/656, 663, 533, 534, 642, 643

(56) References Cited

U.S. PATENT DOCUMENTS 5,255,656  10/1993  Rader et al. .
5,550,478 * 8/1996  Kopera .................................. 324/654
5,608,318 * 3/1997  Yasui .................................... 324/656

* cited by examiner

*Primary Examiner*—Safet Metjahic
*Assistant Examiner*—J Kerveros
(74) *Attorney, Agent, or Firm*—Sughrue, Mion, Zion, Macpeak & Seas, PLLC

(57) ABSTRACT

A dielectric constant sensing device of the present invention comprises a transmission line consisting of a first electrode formed of a conductor being wound like a longitudinal cylinder, a second electrode provided to be separated from the cylindrical surface of the first electrode at a predetermined distance, and a chamber for introducing a measured fluid between the first electrode and the second electrode, whereby a dielectric constant of the measured fluid can be sensed based on a rate of a pulse voltage wave propagated over the transmission line. Accordingly, the fluid dielectric constant sensing device which is able to attain high precision by a simple structure can be provided.

20 Claims, 7 Drawing Sheets

FLUID DIELECTRIC CONSTANT SENSING DEVICE AND METHOD EMPLOYING THE SAME

BACKGROUND OF THE INVENTION

1. Field of the Invention

The present invention relates to a dielectric constant sensing device for sensing a dielectric constant of a fluid to discriminate the property of the fluid and a method employing the same and, more particularly, a device for measuring an alcohol containing rate of an alcohol blended fuel employed in an engine of an automobile, etc. and a method employing the same.

2. Description of the Prior Art

In recent years, in order to promote the employment of the alternative fuel, automobiles which can use the fuel which is prepared by blending alcohol such as methanol, ethanol, etc. into a gasoline are being introduced. If an engine can employ the alcohol blended fuel is controlled, the air-fuel ratio of the engine, the ignition timing, or the like must be changed according to the alcohol concentration in the fuel in order to clean an exhaust gas or to extract a sufficient engine power, unlike the case where an engine can only employ the gasoline is controlled. Since the dielectric constant of the alcohol blended fuel is changed according to the alcohol concentration, the alcohol concentration can be detected by measuring the dielectric constant. For this purpose, in the prior art, for example, the dielectric constant sensing device disclosed in U.S. Pat. No. 5,255,656 has been proposed.

This device will be explained with reference to FIGS. 8, 9, and 10 hereinbelow. FIG. 8 is a plan view, partially broken away, showing a dielectric constant sensing device in the prior art. FIG. 9 is a cross sectional view showing the dielectric constant sensing device in the prior art. FIG. 10 is a block diagram showing a circuit configuration of the dielectric constant sensing device in the prior art.

In FIG. 8, a reference 301 denotes an input pipe into which the fuel is introduced; 302, an output pipe for discharging the fuel; 303, a sensor portion; and 304, a sensor circuit chamber (omitted partially) in which a sensor circuit 400 for processing signals from the sensor portion 303 is built. In FIG. 9, a reference 305 denotes an outer wall of the sensor portion 303 formed of resin, and an electrode 306 which is formed of double layers of copper and nickel by the plating is provided on an entire inner surface of the outer wall 305. A reference 307 denotes a chamber which is filled with the fuel, and a reference 308 denotes a cylindrical coil which is provided in a coaxial manner relative to an inner surface of the outer wall 305 and has the inductance L0. This cylindrical coil operates as an electrode, and has a capacitor of capacitance C0 which is a sum of a stray capacitance formed between the coil wires and a capacitance formed between the electrode 308 and the electrode 306.

In FIG. 10, the electrode 306 is connected electrically to ground of the sensor circuit 400. Both ends of the cylindrical coil 308 are connected to the resonator circuit 401 which is composed of a CMOS inverter. An output of the resonator circuit 401 is connected to the output circuit 402. A reference 403 denotes a power supply circuit 403 for supplying a constant stabilized voltage to the overall sensor circuit, and a reference 404 denotes a temperature measuring circuit which has a thermistor used to execute the temperature compensation.

Next, an operation will be explained. The inductance L0 of the cylindrical coil 308 and the stray capacitance C0 constitute a parallel resonance circuit which can resonate at a resonance frequency Fr given by $$Fr = \frac{1}{2\pi\sqrt{L_0 C_0}} \quad (1)$$

Since the resonance circuit 401 is formed to feed back positively at the resonance frequency Fr, oscillation at the resonance frequency is continued. This resonance frequency is divided by the output circuit 402 and then transmitted to an engine control device (not shown).

If the fuel is filled in the chamber 7, the stray capacitance C0 is changed by the dielectric constant and thus the resonance frequency is changed according to Eq. (1). Therefore, the dielectric constant of the fuel can be detected by sensing the resonance frequency. Since the dielectric constants of the gasoline and the methanol are given as about 2 and about 32 respectively in the methanol blended fuel, change in the methanol concentration contributes significantly to change in the dielectric constant of the fuel. Hence, if the dielectric constant of the fuel can be detected, an alcohol blended ratio can be detected, so that appropriate engine control can be achieved.

However, since the dielectric constant sensing device in the prior art is constructed in the following, there have been problems described later.

Since size of the sensor 3 is not increased so much with regard to the mountability as the engine control device for the automobile, the magnitude of the stray capacitance being formed is limited by itself. In the prior art set forth above, the stray capacitance C0 of the cylindrical coil 308 is only 26 pF. In contrast, the input portion has the stray capacitance having the unnegligible magnitude. For example, if the voltage at the terminal of the cylindrical coil 308 is input into any IC, the input capacitance of several pF exists for every IC. In addition, if the wirings are provided on the circuit substrate, there is the case where the capacitance of several pF is generated only by tne wirings. The stray capacitance at the input portion of the sensor circuit 400 is input in parallel with the stray capacitance C0 of the cylindrical coil 308 in circuit, the stray capacitance C0 is changed correspondingly to thus change the resonance frequency Fr of the sensor.

In addition, such stray capacitance is not a controlled and stabilized capacitance and thus varied easily by the peripheral temperature and the deterioration of the durability. Therefore, there has been the problem that such stray capacitance becomes a factor to cause the error in the sensor output.

In order to employ the cylindrical coil 308 as the inductor as a circuit element, i.e., as a circuit element for generating a voltage, which is proportional to the time differential of the current flowing through the element, between both terminals of the element, both terminals of the cylindrical coil 308 must be connected to the sensor circuit 400. Therefore, there has been the problem that the number of the terminals is increased.

In addition, there has been the problem that, since several electronic parts are needed at the minimum in order to constitute the resonator circuit, a circuit scale is enlarged.

SUMMARY OF THE INVENTION

The present invention has been made to overcome the above problems and it is an object of the present invention to provide a fluid dielectric constant sensing device which is able to attain high precision by a simple structure.

It is another object of the present invention to provide a fluid dielectric constant sensing device which is able to sense a dielectric constant with high precision not to cause re-reflection of a signal.

It is still another object of the present invention to provide a fluid dielectric constant sensing device which is resistant to disturbance.

It is yet still another object of the present invention to provide a fluid dielectric constant sensing device which is resistant to changes in the environment.

It is further object of the present invention to provide a fluid dielectric constant sensing device which is able to sense the dielectric constant in a short time.

It is still further object of the present invention to provide a fluid dielectric constant sensing method which is able to attain high precision simply.

It is yet still further object of the present invention to provide a fluid dielectric constant sensing method which is able to sense a dielectric constant with high precision not to cause re-reflection of a signal.

It is an additional object of the present invention to provide a fluid dielectric constant sensing method which is resistant to changes in the environment.

It is still additional object of the present invention to provide a fluid dielectric constant sensing method which is able to sense the dielectric constant in a short time.

According to an aspect of the present invention, there is provided a fluid dielectric constant sensing device comprising a first electrode formed of a conductor being wound like a longitudinal cylinder; a second electrode separated from the cylindrical surface of the first electrode at a predetermined distance; an introducing portion for introducing a measured fluid between the first electrode and the second electrode; a pulse signal generating means for applying a pulse signal to a transmission line which is composed of the first electrode, the second electrode, and the introducing portion; a pulse signal sensing means for sensing the pulse signal after the pulse signal has propagated over the transmission line; and a dielectric constant sensing means for sensing a dielectric constant of the measured fluid based on a period of time from generation to detection of the pulse signal.

In the fluid dielectric constant sensing device according to the present invention, the first electrode is formed to have a longitudinal cylinder whose a ratio of length/diameter is more than 4.

In the fluid dielectric constant sensing device according to the present invention, an input impedance of the pulse signal sensing means viewed from the transmission line side is set in a range of half to twice of a characteristic impedance of the transmission line.

In the fluid dielectric constant sensing device according to the present invention, the first electrode has an insulating coating of predetermined thickness between the first electrode and the second electrode, and a thickness of the insulating coating is selected to such extent that reflection of the pulse signal is not substantially caused at the pulse signal sensing means.

In the fluid dielectric constant sensing device according to the present invention, a filter means is provided to at least one of the pulse signal generating means and the pulse signal sensing means.

In the fluid dielectric constant sensing device according to the present invention, the filter means is composed of second order filter or high order filter.

In the fluid dielectric constant sensing device according to the present invention, a time required for propagation of the pulse signal over the transmission line is set large to such extent that the time is not affected substantially by variation in a propagation delay time when the pulse signal generating means receives an instruction signal and then responds to the instruction signal, or by variation in the propagation delay time when the pulse signal sensing means receives the pulse signal after the pulse signal has propagated over the transmission line and then responds to the pulse signal.

In the fluid dielectric constant sensing device according to the present invention, a core or a yoke formed of magnetic material is provided to at least one of the first electrode and the second electrode.

In the fluid dielectric constant sensing device according to the present invention, a temperature characteristic of permeability of the core or the yoke has a temperature characteristic which is opposite to that of the dielectric constant of the measure fluid.

In the fluid dielectric constant sensing device according to the present invention, the second electrode has a protection member.

In the fluid dielectric constant sensing device according to the present invention, one end of the first electrode is connected to the pulse signal generating means and other end of the first electrode is opened or connected to a constant voltage portion, and the dielectric constant sensing means senses the dielectric constant of the measure fluid based on a period of time during when the pulse signal being generated by the pulse signal generating means is input from one end of the first electrode and then reflected at the other end to return.

In the fluid dielectric constant sensing device according to the present invention, the pulse signal generating means and the pulse signal sensing means are composed of one Schmidt inverter.

In the fluid dielectric constant sensing device according to the present invention, one end of the first electrode is connected to the pulse signal generating means and other end of the first electrode is connected to the pulse signal sensing means, and the dielectric constant sensing means senses the dielectric constant of the measure fluid based on a period of time during when the pulse signal being generated by the pulse signal generating means is input from one end of the first electrode and then reaches the other end.

In the fluid dielectric constant sensing device according to the present invention, the pulse signal generating means and the pulse signal sensing means are composed of one inverter.

According to another aspect of the present invention, there is provided a fluid dielectric constant sensing method comprising the steps of providing a first electrode formed of a conductor being wound like a longitudinal cylinder and a second electrode provided to be separated from a cylindrical surface of the first electrode at a predetermined distance; forming a signal transmission line as a distributed constant circuit by the first electrode, the second electrode, and a measured fluid introduced between both electrodes; and sensing a dielectric constant or the measured fluid based on an event that a propagation rate of the signal propagated over the transmission line is changed according to an influence which is affected by the dielectric constant of the measured fluid upon a constant of the distributed constant circuit.

In the fluid dielectric constant sensing method according to the present invention, a sensing means for sensing a signal propagated over the transmission line is provided, and difference between a characteristic impedance of the transmission line and an input impedance of the sensing means is adjusted such that the signal is not substantially reflected at an input portion of the sensing means.

In the fluid dielectric constant sensing method according to the present invention, a passage width limiting means for a passage width of the measured fluid being introduced between the first electrode and the second electrode is provided, and the passage width limiting means limits change in the characteristic impedance of the transmission line caused by change in the dielectric constant of the measured fluid.

In the fluid dielectric constant sensing method according to the present invention, a time required for propagation of the pulse signal over the transmission line is set large to such extent that the time is not affected substantially by variation in a propagation delay time when the pulse signal generating means receives an instruction signal and then responds to the instruction signal, or by variation in the propagation delay time when the pulse signal sensing means receives the pulse signal after the pulse signal has propagated over the transmission line and then responds to the pulse signal.

In the fluid dielectric constant sensing method according to the present invention, a propagation rate of the signal propagated over the transmission line is calculated based on a period of time during when the pulse signal being generated by the pulse signal generating means is input from one end of the first electrode and then reflected at the other end to return.

In the fluid dielectric constant sensing method according to the present invention, a propagation rate of the signal propagated over the transmission line is calculated based on a period of time during when the pulse signal being generated by the pulse signal generating means is input from one end of the first electrode and then reaches the other end.

DESCRIPTION OF THE PREFERRED EMBODIMENTS

Embodiments of the present invention will be explained in detail with reference to the accompanying drawings hereinafter.

Embodiment 1

Figure 1:
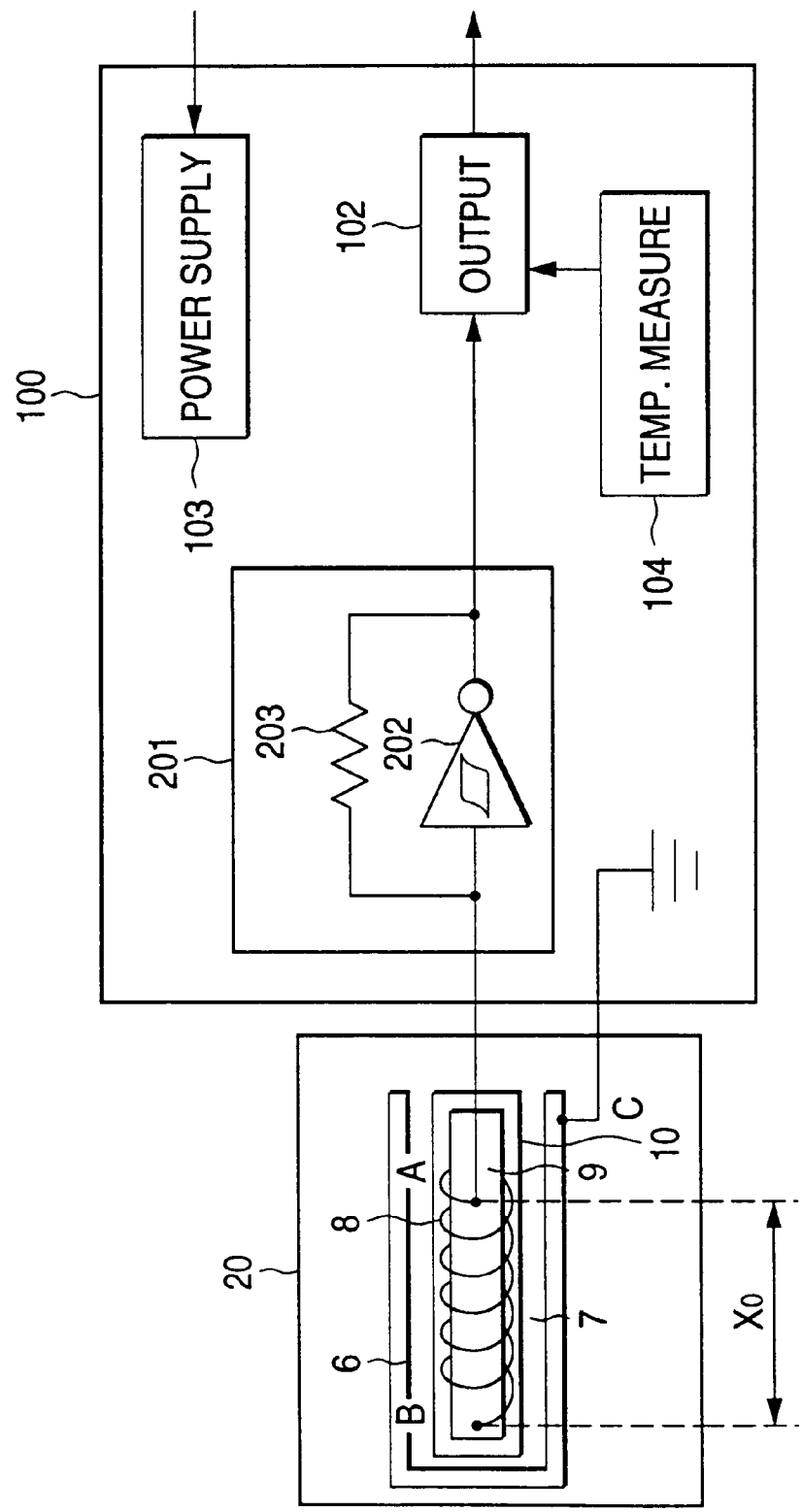
FIG. 1 is a block diagram showing a dielectric constant sensing device according to a first embodiment of the present invention.

FIG. 1 is a schematic block diagram showing a dielectric constant sensing device according to a first embodiment of the present invention. In FIG. 1, a reference 8 denotes a first electrode which is wound on a insulating bobbin 9 to form a longitudinal cylinder. The first electrode 8 is formed of an enameled copper wire which is wound like a longitudinal cylindrical coil. The cylindrical coil has a length of X0=32.5 mm and an outer diameter of 5.9 mm. A reference 10 denotes an insulating coating for covering the first electrode 8. A reference 6 denotes a second electrode which is provided onto a concentric axis apart from an inner surface of the longitudinal cylinder of the first electrode 8 by a constant distance. The second electrode 6 also acts as a metal housing in structure. The second electrode 6 is connected to ground of a sensor circuit 100. A reference 7 is a chamber which is formed by the first electrode 8 and the second electrode 6 and is filled with a measured fluid. The chamber 7 has a function as an introducing portion for introducing the measured fluid between the first electrode 8 and the second electrode 6. The first electrode 8, the second electrode 6, and the chamber 7 constitute a transmission line 20 over which a voltage wave is propagated as a pulse signal.

A point A is an input terminal of the first electrode 8 for the pulse signal and is connected to an oscillator circuit 201 in a sensor circuit 100. A point B is an end point of the first electrode 8 and is electrically opened. Therefore, although the first electrode 8 is formed as a coil, it cannot function as an inductor unlike the prior art, but functions only as one of electrodes constituting the transmission line. The oscillator circuit 201 is composed of a Schmidt inverter 202 and a load resistor 203 of 1 kΩ. An output terminal of the Schmidt inverter 202 acts as a pulse signal generating means. An input terminal of the Schmidt inverter 202 acts as a pulse signal sensing means which senses the voltage wave after it has transmitted over the transmission line. A output of the Schmidt inverter 202 is connected to an output circuit 102. A reference 103 denotes a power supply circuit 103 for supplying a stabilized constant voltage of 5 V to the overall sensor circuit. A reference 104 denotes a temperature measuring circuit 104 which is equipped with a thermistor for executing the temperature compensation of the fluid.

Next, an operational principle of the first embodiment will be explained in brief hereunder.

As described above, the device shown in the prior art constitutes an LC parallel resonator circuit. Since a capacitance value of the resonator circuit is changed according to a dielectric constant of the fuel, the device can sense the dielectric constant of the fuel according to a resonant frequency being correspondingly changed.

Figure 2:
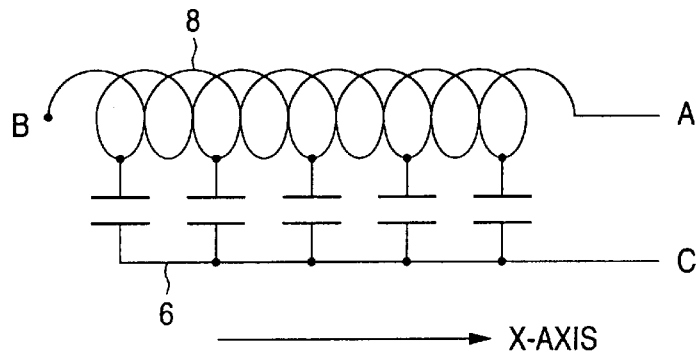
FIG. 2 is a circuit diagram showing an equivalent circuit of a transmission line of the dielectric constant sensing device according to the first embodiment of the present invention.

In contrast, the device shown in FIG. 1 does not employ a resonance phenomenon unlike the device in the prior art, but employs a distributed constant circuit, in which inductors and capacitors are distributed at a constant linear density, as the transmission line. In other words, if the transmission line formed of the distributed constant circuit is employed as a signal propagation route, a propagation rate at which the signal is propagated over the transmission line is affected by the constants of the distributed constant circuit. FIG. 2 shows schematically an equivalent circuit of the transmission line 20 of the dielectric constant sensing device shown in FIG. 1. The transmission line 20 constitutes the distributed constant circuit in which the inductors and the capacitors are distributed at a constant linear density.

An inductance value of the distributed constant circuit in FIG. 2 is decided by the first electrode 8 and is an already known value. A capacitance of the distributed constant circuit is distributed between the first electrode 8 and the second electrode 6. Such capacitance is formed as a capacitor which has the first electrode 8 and the second electrode 6 as electrodes. In this case, the alcohol blended fuel is introduced as the measured fluid between both electrodes of the capacitor. The alcohol blended fuel acts as dielectric substance for the capacitor. A relationship between the capacitance and the dielectric constant of the capacitor is widely known by $$C = \in \cdot S/l \tag{2}$$

In Eq. (2), C is the capacitance, $\in$ is the dielectric constant, S is an area of the electrode, and l is a distance between the electrodes. Since the area S of the electrode and the distance l between the electrodes are fixed, the capacitance C is changed exclusively by the dielectric constant $\in$ of the measured fluid.

Accordingly, the constant of the distributed constant circuit in the transmission line 20 is also changed if the dielectric constant $\in$ of the measured fluid is changed, so that a propagation rate of the signal transmitted over the transmission line 20 is also changed.

As a result, if the propagation rate of the signal transmitted over the transmission line 20 can be sensed, the dielectric constant $\in$ of the measured fluid can be sensed. In this case, since the dielectric constant of the alcohol in the alcohol blended fuel as the measured fluid is extremely large compared to the gasoline, change in the alcohol concentration appears remarkably as a change in the dielectric constant of the alcohol blended fuel. For this reason, the alcohol concentration can also detected if the dielectric constant of the alcohol blended fuel is detected, whereby this information can be employed for engine control.

Then, the first embodiment will be further explained in detail hereunder.

In FIG. 2, since the first electrode 8 is wound to form the longitudinal cylindrical coil along the X-axis direction, the inductance is distributed over the transmission line 20 along the X-axis direction. At the same time, since the first electrode 8 and the second electrode 6 are opposed so as to put the measured fluid therebetween, the capacitance is distributed over the transmission line 20 according to dielectric constant of the measured fluid along the X-axis direction.

It is important that the first electrode 8 is wound like the cylindrical coil. If an aspect ratio (length)/(diameter) of the first electrode 8 is small, the transmission line 20 cannot constitute the distributed constant circuit. As a result, like the prior art, the transmission line 20 must be represented by an equivalent circuit in which the inductance L0 and the capacitance C0 both formed by a-lumped constant respectively are connected in parallel. In addition, since the end point of the first electrode 8 is opened, the inductance does not act and the transmission line 20 acts as a mere capacitor. Hence, a desired operation of the transmission line 20 cannot be attained. However, as depicted by the equivalent circuit in FIG. 2, the distributed constant circuit in which the inductance and the capacitance are distributed at a constant linear density can be constructed by forming the first electrode 8 as the cylindrical coil. According to our experiments, a desired aspect ratio is more than 4 to 5.

In other words, the equivalent circuit shown in FIG. 2 is for the transmission line which is equal to an equivalent circuit of electronic parts for delaying the pulse signal, i.e., a delay line. Such equivalent circuit can propagate the wave at a predetermined propagation rate.

Next, various values of the distributed constant circuit will be explained hereunder.

For simplicity, assume that electric resistance of the first electrode 8 is 0 (zero), the cylindrical shape has a sufficient length to form the distributed constant circuit, an inductance linear density per unit length in the X-axis direction is ρ [H/m], a capacitance linear density is σ [F/m], a linear density of the charge accumulated per unit length is q [C/m], a current is I [A], a voltage is V [V], a position is x [m], and a time is t [sec], then Eq. (3) can be given by $$\delta = -\int \partial I/\partial x \cdot dt \tag{3}$$

from the continuous equation. Also, Eq. (4) can be given by $$q = \sigma V \tag{4}$$

from the equation of capacitance. Also, Eq. (5) can be given by $$\partial V/\partial x = -\rho \cdot \partial I/\partial t \tag{5}$$

from the equation of inductance. By eliminating q and I using Eqs. (3) to (5), then Eq. (6) can be given by $$\frac{\partial^2 V}{\partial t^2} = \frac{1}{\rho\sigma} \cdot \frac{\partial^2 V}{\partial X^2} \tag{6}$$

Since Eq. (6) is a wave equation of the voltage wave, it can be understood that the voltage wave can propagate over this transmission line at the propagation rate U expressed by Eq. (7).

$$U = 1\sqrt{\rho\sigma} \tag{7}$$

Assume that the inductance of the overall transmission line is L0 and the capacitance of the overall transmission line is C0, a time period Tp required to pass the pulse wave over the transmission line can be given-by $$Tp = Xo/U \tag{8}$$

$$= Xo \times \sqrt{\rho\sigma} = Xo \times \sqrt{\frac{Lo}{Xo} \cdot \frac{Co}{Xo}} = \sqrt{Lo \cdot Co}$$

since L0=ρ·X0, C0=σ·X0.

The characteristic impedance Z0 can be expressed by $$Zo = \sqrt{\frac{\rho}{\sigma}} \tag{9}$$

In this embodiment, if ethanol is filled in the chamber 7, measured values are as follows.

Xo=32.5 mm, Lo=29.5 μH, Co=25.2 pF

If Eqs. (7) to (9) are calculated by using these values, values can be given as

ρ=908 μH/m, σ=775 pF/m, U=1190 km/sec, Tp=27 nsec.
Zo=1080Ω

Next, an operation of the first embodiment of the present invention will be explained with reference to FIGS. 3A to 3D hereunder. FIGS. 3A to 3D are graphs showing behavior of the voltage wave in transmission over the transmission line 20.

The dielectric constant sensing device according to the first embodiment operates in the following sequence.

If the voltage at a point A is less than a lower threshold voltage of the Schmidt inverter 202 at time t=0, an output of the Schmidt inverter 202 is risen from 0 V to the power supply voltage 5 V after a delay time Td=about 3.5 nsec in propagation of the Schmidt inverter 202 has lapsed.

The Schmidt inverter 202 constitutes a pulse voltage generating means.

As calculated above, since the characteristic impedance Z0 of the transmission line 20 is about 1 kΩ, the power supply voltage is divided by the load resistance 203 of 1 kΩ and the characteristic impedance Z0 of the transmission line 20 to thus yield about 2.5 V as the voltage at the point A. As described later, the voltage at the point A is held at that value until the reflected wave returns to the point A. An input current flowing into the cransmission line 20 becomes about 2.5 mA which is derived by dividing the voltage at the point A by the characteristic impedance. At this time, since the input of the Schmidt inverter 202 does not exceed an upper threshold voltage, the output of the Schmidt inverter 202 is held at 5 V.

Figure 3A:
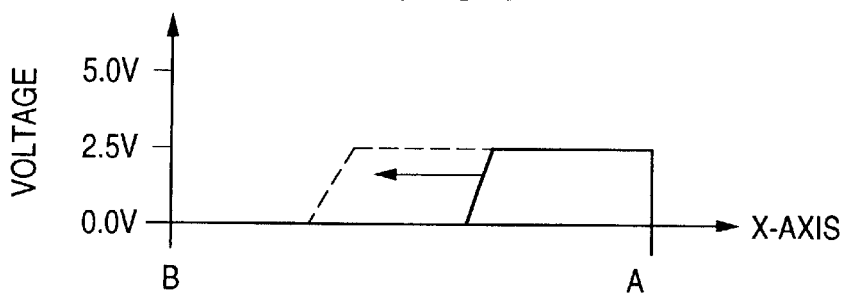
FIGS. 3A to 3D are graphs showing behavior of a voltage wave in transmission over the transmission line of the dielectric constant sensing device according to the first embodiment of the present invention respectively.

As shown in FIG. 3A, a step voltage wave is a pulse signal which has an amplitude of 2.5 V. Such pulse signal propagates as an incident voltage wave from the point A to the point B at a rate U=1190 km/sec. At this time, the right side and the left side of the leading edge of the step voltage wave are uniformly 2.5 V and 0 V respectively. Ideally, the step voltage wave can propagate while keeping its rectangular leading edge at an angle of 90 degrees. Actually, the leading edge of the step voltage wave is inclined according to propagation, as shown in FIG. 3A.

Figure 3B:
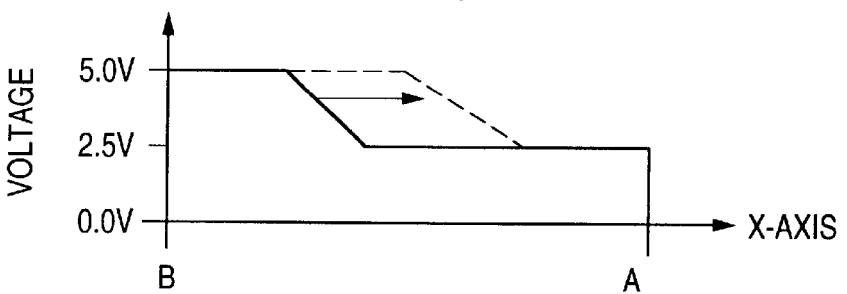

After a time period Tp has lapsed from generation of the step voltage, the leading edge of the step voltage wave comes up to the end point B at a time t1 (=Td+Tp=3.5+27=30.5 nsec). Such voltage wave has such characteristics that its propagation is continued if the characteristic impedance of the transmission line is a substantially identical value, but is reflected there if the characteristic impedance of the transmission line is increased at a certain location. Since the point B is an open end, it corresponds to the infinite impedance. Therefore, as shown in FIG. 3B, the reflected wave of 2.5 V is generated at the point B and then propagates from the point B rightward. As a result, the voltage becomes uniformly 5V in an area where the reflected wave and the incident wave are superposed, i.e., on the left side of the leading edge of the reflected wave, while the voltage becomes uniformly 2.5 V on the right side of the leading edge. The leading edge of the voltage wave is further inclined.

The leading edge of the reflected wave reaches the point A at a time t2 (=Td+2Tp=3.5+2×27=57.7 nsec). At that time, since the voltage at the point A becomes 5 V to exceed the upper threshold voltage of the Schmidt inverter 202, the output of the Schmidt inverter 202 falls from 5 V to 0 V at a time t3 (=2Td+2Tp=2×3.5+2×27=61 nsec) which is delayed by the delay time Td in propagation of the Schmidt inverter 202, whereby incident of the voltage wave is terminated. The Schmidt inverter 202 constitutes a pulse signal sensing means. It is clear that the Schmidt inverter 202 continues to output the incident wave of voltage 2.5 V, which propagates leftward from the point A, until this point of time for Td+2Tp=57.5 nsec.

Since the resistance of 1 kΩ is selected as the load resistance 203, being viewed from the reflected wave, with respect to 1080Ω as the characteristic impedance ZO of the transmission line 20, the impedance matching can be kept substantially between them. Therefore, there seldom occurs such a situation that, when the reflected wave reaches the point A, the reflected wave causes the re-reflection at the point A.

Figure 3C:
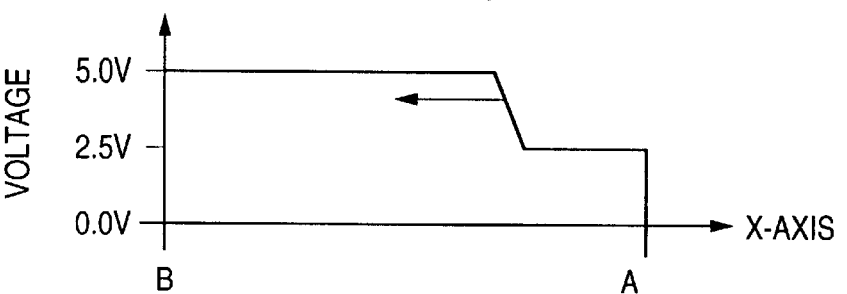

When the output of the Schmidt inverter 202 is changed from 5 V to 0 V to thus terminate the step voltage wave, the trailing edge of the incident wave propagates leftward, as shown in FIG. 3C.

At this time, the voltage becomes uniformly 5 V on the left side of the trailing edge of the incident wave, while the voltage becomes uniformly 2.5 V on the right side of the trailing edge because only the reflected wave remains. Like the leading edge of the step voltage wave, the trailing edge is also inclined with the propagation.

Figure 3D:
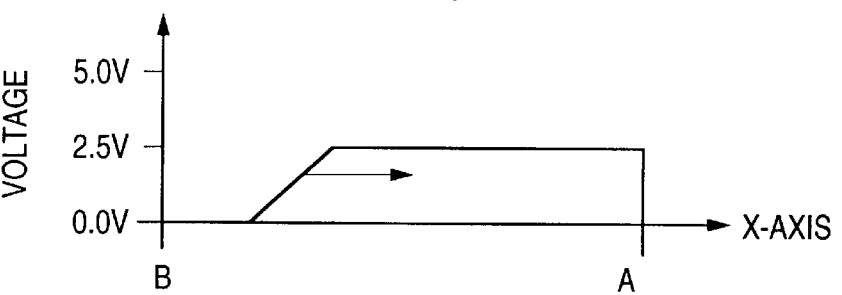

After the trailing edge of the input wave has been reflected at the point B, it propagates rightward, as shown in FIG. 3D.

When the trailing edge of the input wave is reflected and then returns to the point A at a time t4 (=2Td+4Tp=2×3.5+4×27=115 nsec), the voltage of the overall transmission line including the point A becomes uniformly 0 V.

Since the voltage at the point A is less than the lower threshold voltage of the Schmidt inverter 202 when it becomes 0 V, the output of the Schmidt inverter 202 is changed from 0 V to 5 V after the delay time Td (3.5 nsec) in propagation of the Schmidt inverter 202. Then, above operations are repeated after this.

It is understood that, if the dielectric constant of the alcohol blended fuel is large because of the high alcohol concentration, the propagation time Tp of the pulse signal over the transmission line 20 tends to become long since the capacitance CO is increased as calculated by Eq. (8).

Like the above, in the first embodiment, the following period T is repeated and its oscillation frequency F can be given as follows.

$$T = 2Td + 4Tp = 2Td + 4\sqrt{Lo \cdot Co} = 115 \text{ nsec} \qquad (10)$$

$$F = \frac{1}{T} \qquad (11)$$
$$= \frac{1}{(2Td + 4\sqrt{Lo \cdot Co})}$$
$$= \frac{1}{(2Td + 4\sqrt{\rho\sigma})} = 8.7 \text{ MHz}$$

Where the oscillation frequency F is a value associated with the propagation speed at which the signal propagates over the distributed constant circuit. As described above, since the first embodiment is the distributed constant circuit, the oscillation frequency F does not denote the resonance frequency in the prior art. In particular, the premise of the resonance phenomenon is that no delay of the signal exists, but apparently the resonance phenomenon is not caused in the first embodiment since the delay of 2Td exists as indicated by Eq. (10).

This delay of 2Td is due to the delay time in propagation of the Schmidt inverter 202. The Schmidt inverter 202 constitutes a resonance preventing means in the first embodiment.

Figure 4:
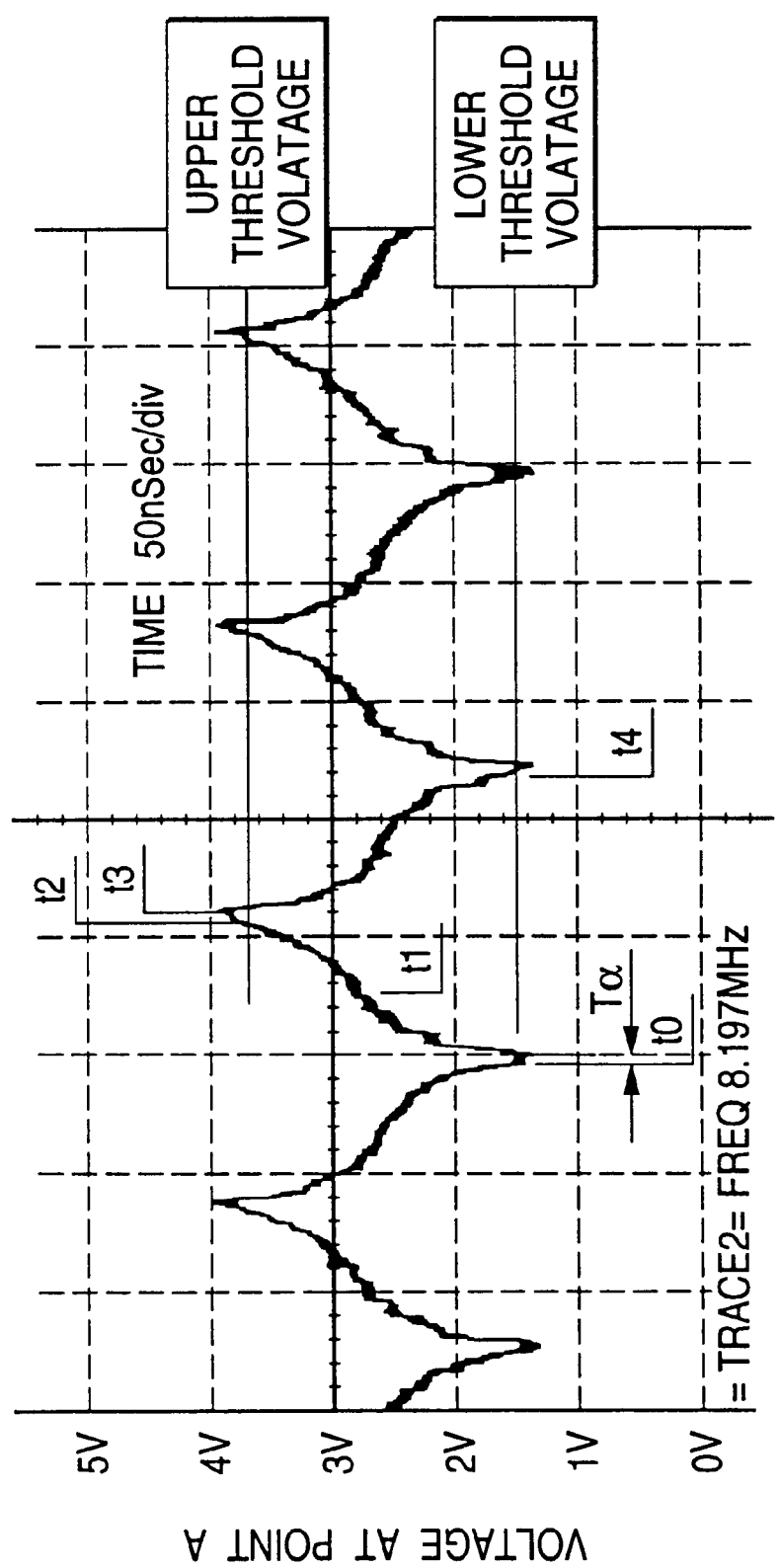
FIG. 4 is a view showing a measured waveform of the voltage wave at an input point of the transmission line of the dielectric constant sensing device according to the first embodiment of the present invention.

FIG. 4 shows a measured waveform of the voltage wave at the point A as an input terminal of the transmission line of the fluid dielectric constant sensing device according to the first embodiment. This measured waveform shows a waveform which supports the above explanation, except that oscillation occurs at a frequency of 8.2 MHz which is slightly lower than that calculated by the above calculation and that an inclination of the waveform is slightly large.

When the fuel is filled in the chamber 7, the inductance linear density ρ is seldom changed, but the capacitance linear density σ is changed according to the dielectric constant of the alcohol blended fuel. At that time, the oscillation frequency F is changed according to Eq. (10). Therefore, the voltage wave propagation rate over the transmission line, the dielectric constant of the fuel, and alcohol blended ratio can be detected by sensing the oscillation frequency F, so that appropriate engine control can be performed.

More particularly, in FIG. 1, the oscillation frequency F sensed by the oscillation circuit 201 is sent out to the output circuit 102 and then is divided at a predetermined ratio in the output circuit 102. In addition to the oscillation frequency F, temperature information of the measured fluid is also sent from the temperature measuring circuit 104 to the output circuit.

The relationship between the alcohol concentration in the alcohol blended fuel and the oscillation frequency F is not always constant, but it has temperature dependency. Therefore, the output circuit 102 divides the oscillation frequency F and corrects the output frequency based on the temperature of the measured fluid, and then outputs them to an engine controlling means (not shown) being composed of a microcomputer, or the like.

The engine controlling means compares the divided oscillation frequency obtained from the output circuit 102 with the frequency detected experimentally in advance based on the alcohol concentration, calculates desired information such as detected alcohol concentration, dielectric constant, or the like in the alcohol blended fuel, and then applies such information to air-fuel ratio control, ignition timing control, or the like.

In the first embodiment, the output circuit 102 is designed to output information of the oscillation frequency being corrected by the temperature of the measured fluid. However, the output circuit 102 may contain a circuit for calculating the dielectric constant based on the oscillation frequency, or a circuit for calculating the alcohol concentration.

Embodiment 2

In the first embodiment, the value of the load resistance 203 is selected such that the impedance matching can be kept between the load resistance 203 and the characteristic impedance Z0 of the transmission line 20 not to cause re-reflection when the pulse signal being propagated over the transmission line enters into the pulse detecting circuit.

It is desired that the value of this load resistance should be set not to deviate by half of the characteristic impedance Z0 of the transmission line 20.

However, since the characteristic impedance Z0 of the transmission line 20 is changed, as indicated by Eq. (9), according to the capacitance linear density σ, i.e., the dielectric constant of the measured fluid in the chamber 7 it is impossible in principle to hold always the impedance matching between the characteristic impedance Z0 and the load resistance 203 perfectly.

However, even in the event that the dielectric constant of the measured fluid is changed in the measuring range, significant influence does not appear if the characteristic impedance Z0 of the transmission line 20 can be set not to deviate by half of the load resistance 203.

In the second embodiment 2, a passage width of the measured fluid flowing between the first electrode 8 and the second electrode 6 is restricted to be narrower by increasing a thickness of an insulating coating 10. The insulating coating 10 functions as a passage width limiting means for limiting the passage width of the measured fluid.

At this time, the insulating coating 10 and the measured fluid function as the dielectric substance between both the first electrode 8 and the second electrode 6. In this case, the capacilance between both electrodes is equivalent to a series circuit of a capacitance using the insulating coating 10 as the dielectric substance and a capacitance 2 using the measured fluid as the dielectric subs-Lance. The capacitance can be given by $$\frac{1}{C} = \frac{1}{\varepsilon_1 \frac{s_1}{l_1}} + \frac{1}{\varepsilon_2 \frac{s_2}{l_2}} \qquad (12)$$

Where the first term of the right side is associated with the capacitance lusing the insulating coating 10 as the dielectric substance, and the second term of the right side is associated with the capacitance 2 using the measured fluid as the dielectric substance.

The capacitance 1 in above Eq. (12) is a fixed value. In the event that a space between both electrodes is almost occupied by a thickness of the insulating coating 10, the value of the capacitance produced between both electrodes is hardly affected even if the value of the capacitance 1 of the first term of the right side is largely changed due to change in the dielectric cons-ant of the measured fluid.

Accordingly, change in the capacitance distributed between both electrodes being caused by the change in the dielectric constant of the measured fluid can be suppressed by increasing the thickness of the insulating coating 10.

Therefore, variation of the characteristic impedance can be reduced by restricting the passage width of the measured fluid, and re-reflection of the pulse signal at the pulse sensing means can be suppressed after the pulse signal has been propagated over the transmission line 20.

In the second embodiment, the passage width of the measured fluid is restricted by changing the thickness of the insulating coating 10. Such restriction is not limited to this, and any means may be employed if the passage width of the measured fluid can be restricted along a distance between both electrodes.

Embodiment 3

Figure 5:
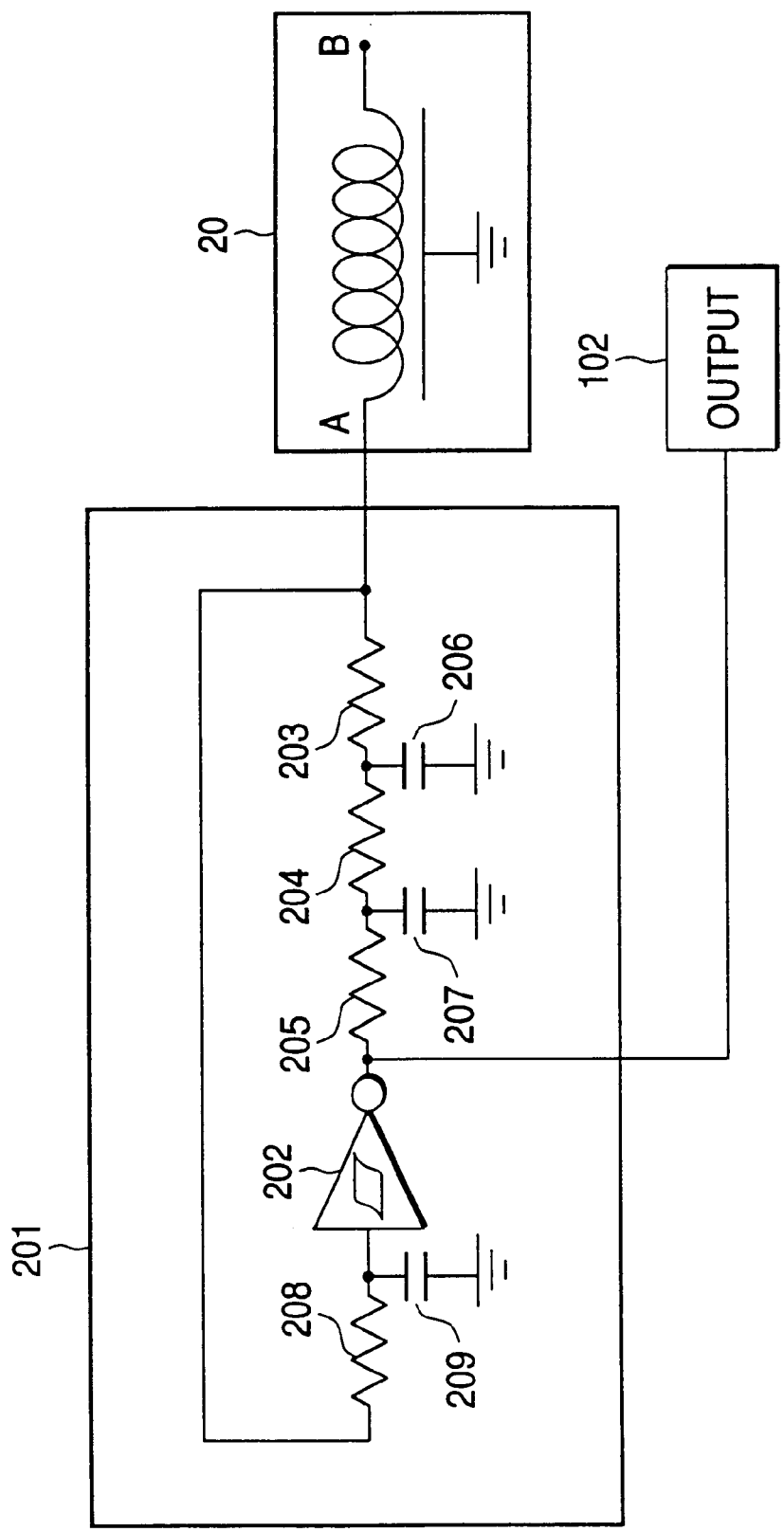
FIG. 5 is a circuit diagram showing an oscillator circuit of a dielectric constant sensing device according to a third embodiment of the present invention.

FIG. 5 is a circuit diagram showing an oscillator circuit of a fluid dielectric constant sensing device according to a third embodiment of the present invention. In the dielectric constant sensing device according to the first embodiment, like the measured waveform shown in FIG. 4, usually it operates normally, but there is the case where the oscillation is caused quasi-stably at another frequency higher than the above fundamental frequency if a large noise is applied. This is because, since the output voltage waveform of the Schmidt inverter has a step-like shape to thus include very high frequency components, sometimes such very high frequency components generate the undesired standing wave over the transmission line 20.

This becomes an issue particularly in the dielectric constant sensing device and method of the present invention. More specifically, as described in the first embodiment, sensing of the dielectric constant is executed by detecting the propagation of the pulse signal from its rise to its fall. Therefore, if noises are generated during when the pulse signal is generated to thus cause falling of the pulse signal, there is a possibility that such pulse signal is detected erroneously as a very short pulse to thereby cause an error in sensing the dielectric constant.

Therefore, in the third embodiment, as shown in FIG. 5, such high frequency components can be absorbed by adding a filter the oscillator circuit.

In FIG. 5, the output side of the Schmidt inverter 202 is formed in a multi-stage fashion. The output side of the Schmidt inverter 202 constitutes a second order filter in FIG. 5.

In the third embodiment, if the filter which is provided to the input side or the output-side of the Schmidt inverter 202 is formed as a high order filter such as second order filter or more, the oscillation at the frequency other than the fundamental frequency can be prevented particularly effectively.

There is no event that, if the high order filter is employed, the leading edge or trailing edge of the pulse signal is not rounded excessively. As a result, the dielectric constant can be detected with high precision.

Embodiment 4

As expressed by Eqs. (10) and (11), the delay time Td in propagation of the Schmidt inverter 202 has an influence upon the oscillation frequency F. However, since stability of Td cannot be expected against the change in temperature and the change in durability, variation in the oscillation frequency F is caused. Therefore, in order to reduce the influence of unstable variantion of Td, it is effective to increase the time Td, which the pulse signal needs to pass through over the transmission line, as long as possible by increasing the inductance linear density $\rho$ or the capacitance linear density $\sigma$ of the transmission line.

Magnetic material can be employed as one approach of increasing the above time Tp.

Figure 6:
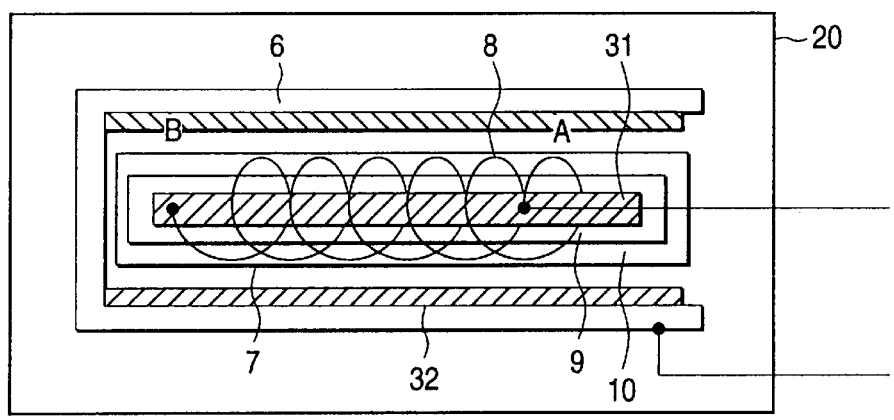
FIG. 6 is a block diagram showing a transmission line of a dielectric constant sensing device according to a fourth embodiment of the present invention.
Figure 8:
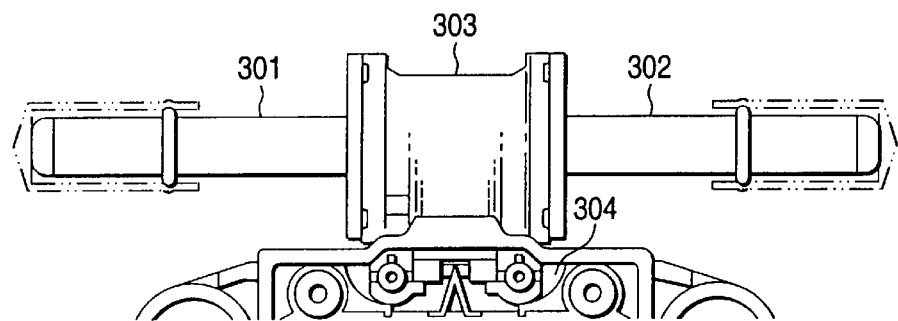
FIG. 8 is a plan view, partially broken away, showing a dielectric constant sensing device in the prior art.

FIG. 6 is a schematic block diagram showing a transmission line 20 of a dielectric constant sensing device according to a fourth embodiment of the present invention. In FIG. 6, a reference 31 denotes a core which is formed of soft magnetic material and is installed in the bobbin 9, and a reference 32 denotes a yoke which is also formed of soft magnetic material and is provided on the outside of the first electrode 8. The inductance linear density $\rho$ of the transmission line 20 can be enhanced by providing these core and yoke to thus prolong the time Tp.

Normally the dielectric constant of the fluid has the temperature characteristic. However, if the core and the yoke, the temperature characteristic of the permeability of which is opposite to that of the dielectric constant of the measured fluid, is employed, the influence of the change in temperature of the dielectric constant of the fluid can be canceled.

Embodiment 5

In the dielectric constant sensing device according to the first to fourth embodiments, the turnaround time of the voltage wave over the transmission line is measured by employing the reflection of the voltage wave generated a the end point of the transmission line. This method is very available in improving the detection precision of the dielectric constant since the pulse signal travels back and forth over the transmission line and therefore the time required for propagation can be set very long rather than the delay time Td in propagation of the Schmidt inverter 202.

However, in case the length XO of the coil of the first electrode 6 is set sufficiently long, or adequate detection precision is provided by adding the yoke, the core, etc. in the fourth embodiment, the propagation time required for one way over the transmission line may be detected not to cause the reflection of the pulse signal.

Figure 7:
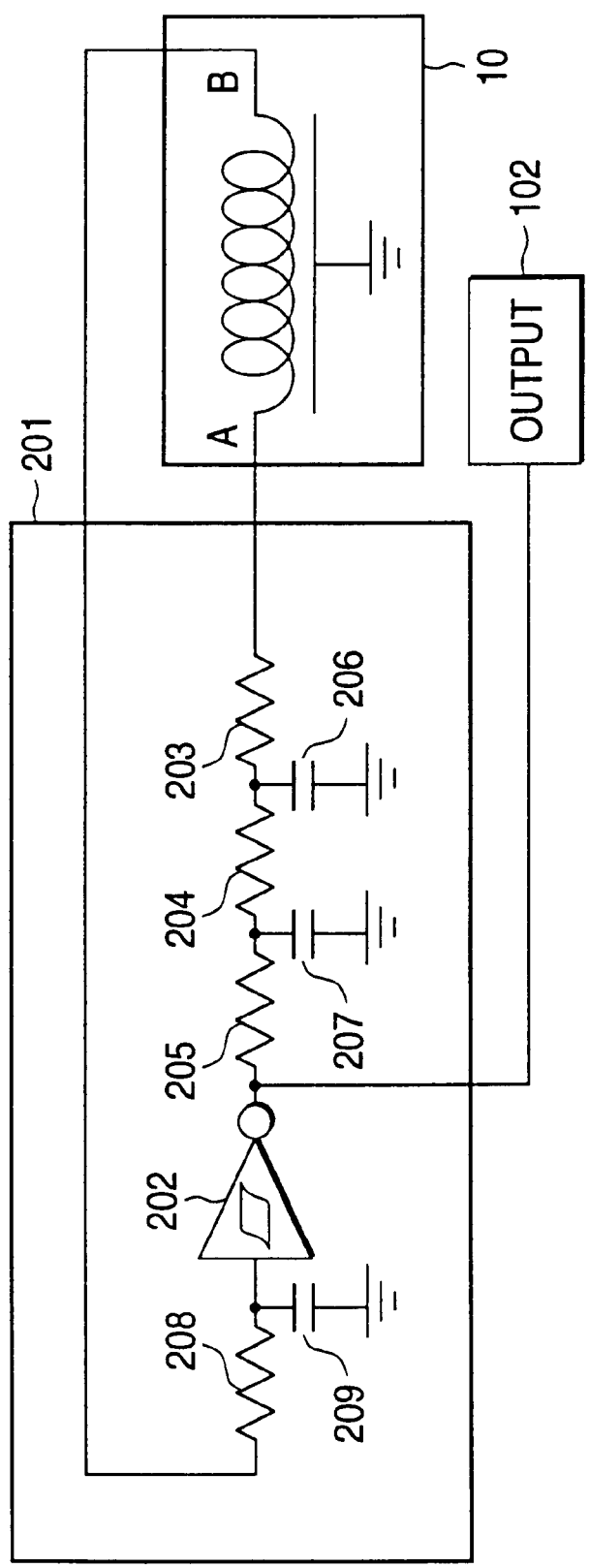
FIG. 7 is a circuit diagram showing an oscillator circuit of a dielectric constant sensing device according to a fifth embodiment of the present invention.
Figure 9:
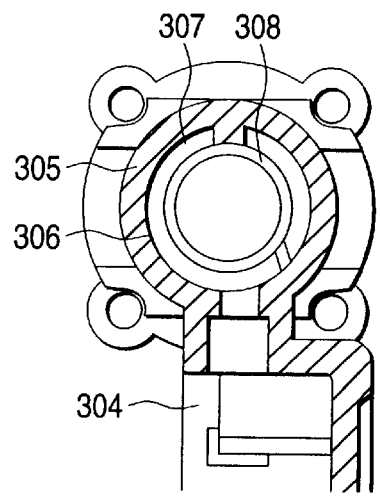
FIG. 9 is a cross sectional view showing the dielectric constant sensing device in the prior art.
Figure 10:
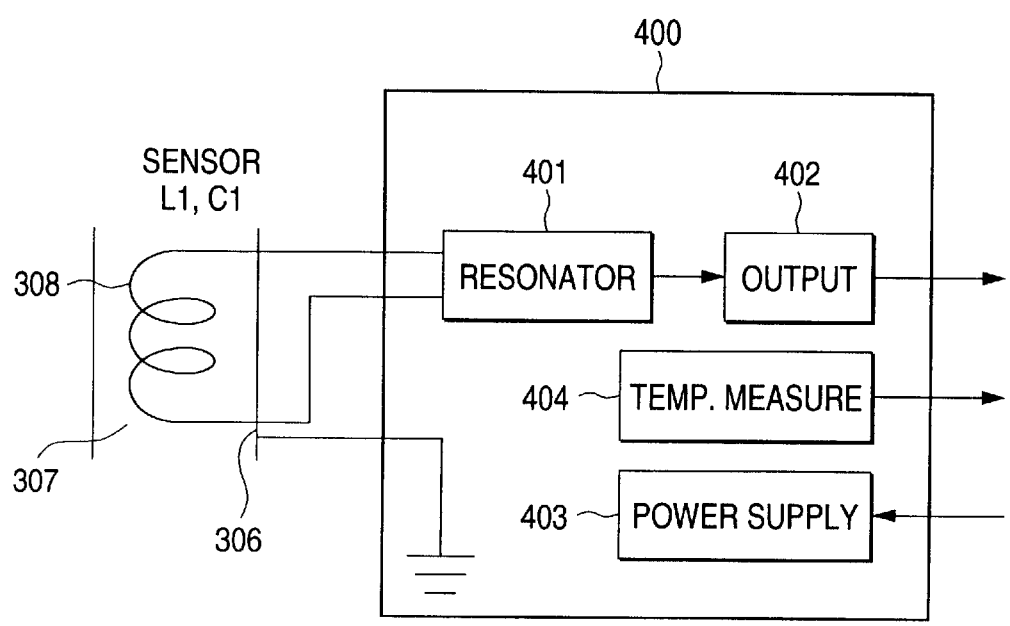
FIG. 10 is a block diagram showing a circuit configuration of the dielectric constant sensing device in the prior art.

FIG. 7 is a circuit diagram showing an oscillator circuit of a dielectric constant sensing device according to a fifth embodiment of the present invention. This circuit resembles the circuit in the second embodiment shown in FIG. 5, but is different in that the voltage being input into the input terminal of the Schmidt inverter 202 serving as the pulse signal sensing means is picked up from the point B of the output end of the transmission line 20 in place of the point A of the input end.

When the output of the Schmidt inverter 202 rises from 0 V to 5 V, the voltage wave as the pulse signal propagates from the point A to the point B, whereby the voltage at the input terminal of the Schmidt inverter 202 is rendered to exceed the threshold voltage. At that time, the output of the Schmidt inverter 202 rises. Then, the voltage wave falls from 5 V to 0 V to propagate from the point A to the point B, whereby the voltage at the input terminal of the Schmidt inverter 202 is rendered to decrease below the threshold voltage. Therefore, the output of the Schmidt inverter 202 rises from 0 V to 5 V. The propagation rate of the voltage wave can be detected by measuring such repetition frequency and as a result the dielectric constant of the measured fluid can be sensed, like the above embodiments.

According to the fifth embodiment, although the pulse signal propagates over the transmission line 20 merely by one way, the dielectric constant of the measured fluid can be sensed similarly as in the case where the pulse signal propagates reciprocally.

In the fifth embodiment, the normal inverter may be employed instead of the Schmidt inverter.

In other words, in the above embodiments, if it is attempted to input the pulse signal to the pulse signal sensing means without re-reflection after it has propagated over the transmission line 20, first the impedance matching between the transmission line 20 and the load resistance 203 must be taken. Then, the pulse signal is sensed from a connecting point (point A) between the transmission line 20 and the load resistance 203. Therefore, the voltage at the point A is reduced to the half (2.5 V) of the power supply voltage until the reflection wave returns to the point B of the first electrode from generation of the pulse signal by the inverter. Since the change in the output of the inverter during this period is not desirable in the above embodiments, for example, the Schmidt inverter whose output does not exceed the upper threshold voltage such as 2.5 V, etc. must be provided.

On the contrary, in the fifth embodiment, since the pulse signal propagates over the transmission line 20 only by one way, the output terminal of the inverter can be connected the point A of transmission line 20 and simultaneously the input terminal of the inverter can be connected to the point B of the transmission line 20.

Therefore, the normal inverter whose upper or lower threshold voltage is set near 2.5 V with respect to the power supply voltage 5 V may be employed.

In this case, since the normal inverter has the shorter delay time in propagation rather than the Schmidt inverter, the dielectric constant of the measured fluid can be detected more quickly.

In addition, although the second electrode is not covered with a protection member in the above embodiments, such second electrode may be covered with the protection member if protection is needed against the electric insulation and the corrosion.

If the pulse signal propagates reciprocally over the transmission line in the above embodiments, the point B or the first electrode 8 is set as the open terminal. However, the point B of the first electrode 8 may be connected to a constant voltage portion such as the power supply terminal, the ground, etc. In brief, the characteristic impedance of the transmission line 20 and the impedance at the point B are differentiated with each other to such extent that the reflection of the signal can be caused.

As described above, according to the fluid dielectric constant sensing device according to the present invention, there is provided a fluid dielectric constant sensing device comprising a first electrode formed of a conductor being wound like a longitudinal cylinder, a second electrode provided in an inside of a cylindrical surface to be separated from the cylindrical surface of the first electrode at a predetermined distance, an introducing portion for introducing a measured fluid between the first electrode and the second electrode, a pulse signal generating means for applying a pulse signal to a transmission line which is composed of the first electrode, the second electrode, and the introducing portion, a pulse signal sensing means for sensing the pulse signal after the pulse signal has propagated over the transmission line, and a dielectric constant sensing means for sensing a dielectric constant of the measured fluid based on a period of time from generation to detection of the pulse signal. Therefore, the fluid dielectric constant sensing device which is able to attain high precision by a simple structure can be provided.

According to the fluid dielectric constant sensing device according to the present invention, the fluid dielectric constant sensing device which is able to sense a dielectric constant with high precision not to cause re-reflection of a signal can be provided.

According to the fluid dielectric constant sensing device according to the present invention, the fluid dielectric constant sensing device which is resistant to disturbance can be provided.

According to the fluid dielectric constant sensing device according to the present invention, the fluid dielectric constant sensing device which is resistant to changes in the environment can be provided.

According to the fluid dielectric constant sensing device according to the present invention, the fluid dielectric constant sensing device which is able to sense the dielectric constant in a short time can be provided.

According to the fluid dielectric constant sensing method according to the present invention, the fluid dielectric constant sensing method which is able to attain high precision simply can be provided.

According to the fluid dielectric constant sensing method according to the present invention, the fluid dielectric constant sensing method which is able to sense a dielectric constant with high precision not to cause re-reflection of a signal can be provided.

According to the fluid dielectric constant sensing method according to the present invention, the fluid dielectric constant sensing method which is resistant to changes in the environment can be provided.

According to the fluid dielectric constant sensing method according to the present invention, the fluid dielectric constant sensing method which is able to sense the dielectric constant in a short time can be provided.

What is claimed is:

1. A fluid dielectric constant sensing device comprising:
   a first electrode formed of a conductor being wound like a longitudinal cylinder;
   a second electrode separated from the cylindrical surface of the first electrode at a predetermined distance;
   an introducing portion for introducing a measured fluid between the first electrode and the second electrode;
   a pulse signal generating means for applying a pulse signal to a transmission line which includes the first electrode, the second electrode, and the introducing portion;
   a pulse signal sensing means for sensing the pulse signal after the pulse signal has propagated over the transmission line; and
   a dielectric constant sensing means for sensing a dielectric constant of the measured fluid based on a period of time from generation of the pulse signal to detection of the pulse signal by the pulse signal sensing means.

2. The fluid dielectric constant sensing device of claim 1, wherein the first electrode is formed to have a longitudinal cylinder whose a ratio of length/diameter is more than 4.

3. The fluid dielectric constant sensing device of claim 1, wherein an input impedance of the pulse signal sensing means viewed from the transmission line side is set in a range of half to twice of a characteristic impedance of the transmission line.

4. The fluid dielectric constant sensing device of claim 3, wherein the pulse signal generating means and the pulse signal sensing means comprises one inverter.

5. The fluid dielectric constant sensing device of claim 1, wherein the first electrode has an insulating coating of predetermined thickness between the first electrode and the second electrode, and a thickness of the insulating coating is selected to such extent that reflection of the pulse signal is not substantially caused at the pulse signal sensing means.

6. The fluid dielectric constant sensing device of claim 1, wherein a filter means is provided to at least one of the pulse signal generating means and the pulse signal sensing means.

7. The fluid dielectric constant sensing device of claim 6, wherein the filter means is composed of second order filter or high order filter.

8. The fluid dielectric constant sensing device of claim 1, wherein a time required for propagation of the pulse signal over the transmission line is set large to such extent that the time is not affected substantially by variation in a propagation delay time when the pulse signal generating means receives an instruction signal and then responds to the instruction signal, or by variation in the propagation delay time when the pulse signal sensing means receives the pulse signal after the pulse signal has propagated over the transmission line and then responds to the pulse signal.

9. The fluid dielectric constant sensing device of claim 8, wherein a core or a yoke formed of magnetic material is provided to at least one of the first electrode and the second electrode.

10. The fluid dielectric constant sensing device of claim 8, wherein a temperature characteristic of permeability of the core or the yoke has a temperature characteristic which is opposite to that of the dielectric constant of the measure fluid.

11. The fluid dielectric constant sensing device of claim 1, wherein the second electrode has a protection member.

12. The fluid dielectric constant sensing device of claim 1, wherein one end of the first electrode is connected to the pulse signal generating means and other end of the first electrode is opened or connected to a constant voltage portion, and the dielectric sensing means senses the dielectric constant of the measured fluid based on a period of time during which the pulse signal being generated by the pulse signal generating means is input from a first end of the first electrode and then reflected at the other end of the first electrode to return to the first end of the first electrode.

13. The fluid dielectric constant sensing device of claim 1, wherein the pulse signal generating means and the pulse signal sensing means are composed of one Schmidt inverter.

14. The dielectric constant sensing device of claim 1, wherein one end of the first electrode is connected to the pulse signal generating means and the other end of the first electrode is connected to the pulse signal sensing means, and the dielectric constant sensing means senses the dielectric constant of the measured fluid based on a period or time during which the pulse signal being generated by the pulse signal generating means is input from one end of the first electrode and then reaches the other end of the first electrode.

15. A fluid dielectric constant sensing method comprising the steps of:

providing a first electrode formed of a conductor being wound as a longitudinal cylinder and a second electrode provided to be separated from a cylindrical surface of the first electrode at a predetermined distance;

forming a signal transmission line as a distributed constant circuit by the first electrode, the second electrode, and a measured fluid introduced between the first and second electrodes; and sensing a dielectric constant of the measured fluid based on a change in propagation rate of the signal propagated over the transmission line caused by an affect of the dielectric constant of the measured fluid upon a constant of the distributed constant circuit.

16. The fluid dielectric constant sensing method of claim 15, wherein a sensing means for sensing a signal propagated over the transmission line is provided, and difference between a characteristic impedance of the transmission line and an input impedance of the sensing means is adjusted such that the signal is not substantially reflected at an input portion of the sensing means.

17. The dielectric constant sensing method of claim 15, wherein a passage width limiting means for a passage width of the measured fluid being introduced between the first electrode and the second electrode is provided, and the passage width limiting means limits change in the characteristic impedance of the transmission line caused by change in the dielectric constant of the measured fluid.

18. The fluid dielectric constant sensing method of claim 15, wherein a time required for propagation of the pulse signal over the transmission line is set large to such extent that the time is not affected substantially by variation in a propagation delay time when the pulse signal generating means receives an instruction signal and then responds to the instruction signal, or by variation in the propagation delay time when the pulse signal sensing means receives the pulse signal after the pulse signal has propagated over the transmission line and then responds to the pulse signal.

19. The fluid constant sensing method of claim 15, wherein a propagation rate of the signal propagated over the transmission line is calculated based on a period of time during which the pulse signal generated by the pulse signal generating means is input from a first end of the first electrode and then reflected at the other end to return to the first end of the first electrode.

20. The fluid dielectric constant sensing method of claim 15, wherein a propagation rate of the signal propagated over the transmission line is calculated based on a period of time during which the pulse signal being generated by the pulse signal generating means is input from one end of the first electrode and then reaches the other end of the first electrode.

* * * * *